United States Patent
Kratschmer et al.

(10) Patent No.: US 9,310,297 B2
(45) Date of Patent: Apr. 12, 2016

(54) METHOD FOR DETERMINING AT LEAST ONE PHYSICAL, CHEMICAL AND/OR BIOLOGICAL MEASURED VARIABLE BY MEANS OF OPTICAL SENSORS, AND TURBIDITY SENSOR

(71) Applicant: Endress + Hauser Conducta Gesellschaft für Mess—und Regeltechnik mbH + Co. KG, Gerlingen (DE)

(72) Inventors: Thilo Kratschmer, Gerlingen (DE); Matthias Grossmann, Vaihingen-Enz (DE); Carsten Gotz, Ettenheim (DE)

(73) Assignee: Endress + Hauser Conducta Gesellschaft für Mess—und Regeltechnik mbH + Co. KG, Gerlingen (DE)

( * ) Notice: Subject to any disclaimer, the term of this patent is extended or adjusted under 35 U.S.C. 154(b) by 0 days.

(21) Appl. No.: 14/509,337

(22) Filed: Oct. 8, 2014

(65) Prior Publication Data

US 2015/0103344 A1 Apr. 16, 2015

(30) Foreign Application Priority Data

Oct. 16, 2013 (DE) .......................... 10 2013 111 416

(51) Int. Cl.
| | |
|---|---|
| *G01N 21/00* | (2006.01) |
| *G01N 21/53* | (2006.01) |
| *G01N 15/06* | (2006.01) |
| *G01N 21/27* | (2006.01) |

(52) U.S. Cl.
CPC ................ *G01N 21/53* (2013.01); *G01N 15/06* (2013.01); *G01N 21/274* (2013.01); *G01N 2015/0693* (2013.01)

(58) Field of Classification Search
CPC .......... G01N 2015/0693; G01N 15/06; G01N 21/274; G01N 21/53
See application file for complete search history.

(56) References Cited

U.S. PATENT DOCUMENTS

| | | | |
|---|---|---|---|
| 6,112,157 A * | 8/2000 | Boon et al. ....................... | 702/58 |
| 6,573,991 B1 * | 6/2003 | Debreczeny et al. .......... | 356/336 |
| 2004/0027569 A1* | 2/2004 | Tucker .......................... | 356/338 |
| 2006/0198761 A1 | 9/2006 | Tokhtuev | |

(Continued)

FOREIGN PATENT DOCUMENTS

| | | |
|---|---|---|
| DE | 19828868 A1 | 5/2000 |
| DE | 102008047467 A1 | 3/2010 |

OTHER PUBLICATIONS

German Search Report, German PTO, Munich, Oct. 16, 2014.

*Primary Examiner* — Kara E Geisel
*Assistant Examiner* — Shawn Decenzo
(74) *Attorney, Agent, or Firm* — Bacon & Thomas, PLLC

(57) ABSTRACT

A turbidity sensor and a method for determining at least one physical, chemical and/or biological measured variable of process automation in a medium by means of at least one optical sensor, comprising the steps of sending transmission signals into the medium, wherein the transmission signals are converted into received signals by interaction with, especially by scattering from, the medium as a function of the measured variable; receiving the received signals; and converting the received signals into the measured variable as a function of environmental conditions at the location of installation and, adjusting the sensor based on a calibration graph corresponding to environmental conditions at the location of installation.

11 Claims, 1 Drawing Sheet

(56) References Cited

U.S. PATENT DOCUMENTS

| | | | |
|---|---|---|---|
| 2009/0059218 A1* | 3/2009 | Harner et al. | 356/243.2 |
| 2010/0073173 A1* | 3/2010 | Zindy et al. | 340/627 |
| 2012/0205547 A1* | 8/2012 | Klinkhammer | G01N 21/0303 250/373 |
| 2014/0234952 A1* | 8/2014 | Moore | 435/288.7 |

* cited by examiner

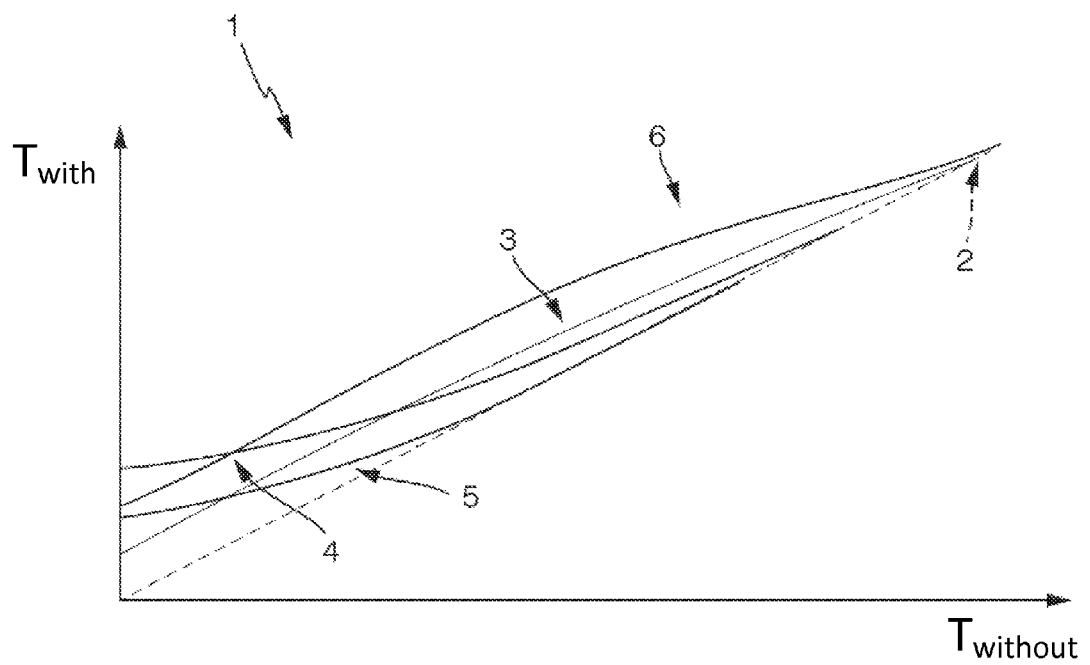

METHOD FOR DETERMINING AT LEAST ONE PHYSICAL, CHEMICAL AND/OR BIOLOGICAL MEASURED VARIABLE BY MEANS OF OPTICAL SENSORS, AND TURBIDITY SENSOR

TECHNICAL FIELD

The invention relates to a method for determining at least one physical, chemical and/or biological measured variable of process automation in a medium by means of optical sensors. The invention relates further to a turbidity sensor for performing the method.

BACKGROUND DISCUSSION

An optical measured variable of process automation is, for example, the turbidity of a medium. In the following, the posed problem will be explained without limitation based on this measured variable.

Optical turbidity determination rests on scattered light measurement from undissolved particles suspended in the medium to be measured. In the case of use of turbidity sensors in containments, thus, for example, in pipelines or flow-through cells, wall effects lead to corruption of measured values. The light reflected or scattered on the inner surface of the pipe wall is detected by the sensor and incorrectly interpreted as a turbidity signal. A technique for minimizing these wall effects in pipelines involves an optimized sensor design (see, for example, the as yet unpublished application German DE 10 2013 103 735).

In order to minimize the undesired scattering on the tube, or pipe, wall, black, non-reflecting surfaces or larger dimensions of the pipeline can be used. This is, however, due to cost- or space reasons, not always possible. Also, frequently, a certain material must be used, for instance, for hygienic applications.

Even with the above mentioned improvements, one cannot, as a rule, completely remove the influence of wall effects on the measured value, above all, in the case of small tube diameters, respectively small wall separations and/or reflecting materials.

Since the influence of the wall effects changes with the turbidity value (wall effects have, as a rule, a greater influence in the case of lesser cloudings; wall effects have, as a rule, lesser influence in the case of greater cloudings), it is for the user very difficult and very complex to eliminate these effects by means of calibration. The user would have to perform comparative measurements at a number of turbidity values, and these are often error susceptible, time intensive and expensive, or bring about a state, which, as a rule, cannot be synthetically generated. Thus, in real systems, turbidity values cannot be varied as much as desired.

SUMMARY OF THE INVENTION

An object of the invention is to improve optical measuring methods, wherein especially the unknown influence of wall effects is taken into consideration. In other words, wall effects should be compensated by suitable adjustment of the sensor.

The object is achieved by a method comprising steps of sending transmission signals into the medium, wherein the transmission signals are converted into received signals by interaction with, especially by scattering from, the medium as a function of the measured variable; receiving the received signals; and converting the received signals into the measured variable as a function of environmental conditions at the location of installation, and wherein the sensor is adjusted based on a calibration graph corresponding to environmental conditions at the location of installation. The terminology "graph" in the sense of this invention is meant to include a table, function, formula, actual graph and the like.

The terminology "adjust" in the sense of this invention means a correlating of the true measured value with the actual measured value.

Calibration graphs of possible environmental conditions are earlier established, for example, by the offeror or manufacturer. The user then selects its suitable set of environmental conditions, most often, directly on-site. The user, thus, does not need to perform complicated calibrating with adjusting, but, instead, can rely on the calibration graphs appropriate for the environmental conditions present at its measuring point.

In an advantageous form of embodiment, the calibration graph is created by steps as follows: calibrating the sensor multiple times under respectively different environmental conditions, wherein the environmental conditions concern at least different materials and different diameters of a calibration containment, respectively different distances to a calibration containment, wherein the calibrating is performed for different values of the measured variable; and recording calibration graphs corresponding to different environmental conditions, wherein the corresponding environmental conditions of the location of installation are selected, and wherein the sensor is adjusted based on environmental conditions at the location of installation according to a corresponding calibration graph.

In an advantageous embodiment, the optical sensor is a turbidity sensor and the measured variable is turbidity. Another advantageous embodiment is a sensor for determining a particle or ion concentration. Another advantageous embodiment is a conductivity sensor. Another advantageous embodiment is a temperature sensor. In all these cases, a wall disturbs and can negatively influence the measuring (reflections lead to incorrect measurement results, particles or ions clinging to wall, conductivity is different at the wall, temperature of the medium is different from the temperature of the wall).

Preferably and in order to cover the appropriate turbidity value range, the calibrating is performed for turbidity values from 0 FNU to 500 FNU. Depending on material and diameter/separation, different increments are selected. Thus, in the case of smaller turbidity values, a smaller increment is selected, for example, 0.5 FNU; in the case of greater turbidity values, a greater increment is selected, for example, 30 FNU.

Advantageously, the materials are selected from a list including at least stainless steel, cast-iron, copper, polyethylene (PE), polyvinyl chloride (PVC), polypropylene (PP), glass fiber reinforced plastics (GFP), brass and ceramics.

In an advantageous form of embodiment, the environmental conditions further include surface roughness, surface color, texture of the surface and/or accretions.

Preferably, the diameter lies in the range of nominal diameters DN10 to DN1000 in the case of an application in pipes or tubes. In the case of an application in a vat or the like, the separation is preferably in the range of values from 10 mm to 1000 mm. Depending on type of sensor, however, also smaller diameters/separations provide options. Temperature sensors are, for example, applicable in containments with yet smaller diameters/separations. Also, biological or chemical sensors, so called lab on a chip sensors, can be used in smaller diameters/with smaller separations. Also, fiber coupled sensors are used in pipes with smaller diameters, respectively in containments with lesser wall separations. There are turbidity sensors available, which in and out couple the light with light conductors ("optical fibers").

The object is further achieved by a turbidity sensor for performing the method according to at least one of the above described embodiments.

In a preferred embodiment, a superordinated unit is provided, in which the calibration graphs are stored, and wherein through the superordinated unit the corresponding environmental conditions are selected, wherein the superordinated unit is part of the sensor or is installed in an external device, especially in a transmitter. Thus, an easy way is provided for selecting the appropriate environmental conditions.

In an advantageous form of embodiment, the turbidity sensor is connected with the transmitter via a galvanically isolated, especially inductive, interface.

BRIEF DESCRIPTION OF THE DRAWINGS

The invention will now be explained in greater detail based on the appended drawing, the sole FIGURE of which shows a typical calibration graph.

DETAILED DISCUSSION IN CONJUNCTION WITH THE DRAWING

An application of the method of the invention is for turbidity measurement. Of course, the method is also applicable for other optical measuring methods, in the case of which the mentioned problems occur. Examples of other applications include temperature sensors, conductivity sensors, sensors for measuring particle or ion concentration and lab on a chip sensors (biological or chemical). Since turbidity measurement is basically known, such measuring principle will be only briefly reviewed.

For turbidity measurement, a light beam is sent through the medium, where it is deflected from its original direction by optically denser components, e.g. by solid particles. This behavior is referred to as scattering. The light is scattered in many directions, thus at different angles relative to the original direction. In such case, two angular regions are of greatest interest: The scattered light registered at an angle of 90° relative to the direction of the sent light is only little influenced by the particle size. The other scatter angle of interest is 135° relative to the incidence direction. This light in the 135°-direction gives information in the case of high particle densities. If the particle density in the medium is small, much light is scattered to the 90°-channel and little light to the 135°-channel. If the particle density rises, this relationship shifts (more light to the 135°-channel, less light to the 90°-channel). An established turbidity sensor uses two sensor units, which are independent of one another and arranged parallel to one another. The application dependent evaluation of the two signals leads to stable, measured values. In this way, optimal turbidity- and solids measurement is possible. In the case of low turbidity values, preferably the 90°-channel is used. In the case of middle and high turbidity values as well as for solids measurements, the 135°-channel is used.

There are essentially four methods of measuring, the multi-beam, alternating light method, the 90°-scattered light method, the forwards scattered light method and the back scattered light method.

The four beam, alternating light method, as one version of the multi-beam, alternating light method, uses two light sources and two light receivers. Used as monochromatic light sources are light-emitting diodes with high lifetimes. These light-emitting diodes are alternately pulsed and produce then per LED-pulse, in each case, two scattered light signals at the receivers. Disturbing influences such as stray light, aging of the LEDs, window dirt and absorption in the medium are compensated in this type of operation. Depending on selected model, different scattered light signals are taken into consideration, wherein the type, number and compensation of the signals are furnished in the sensor.

In the 90°-scattered light method, the measuring occurs with a wavelength of 860 nm, such as specified in ISO 7027/EN 27027. The incident light beam is scattered by the solid particles in the medium. The so produced scattered radiation is measured via scattered light receivers, which are arranged at an angle of 90° relative to the light sources. The turbidity of the medium is ascertained from the amount of scattered light.

In the back scattered light method, the incident light beam is scattered by the solid particles in the medium. The produced back scattering is measured via scattered light receivers. The turbidity of the medium is ascertained via the amount of backscattered light. With this form of scattered light measurement, very high turbidity values can be measured.

These three measuring methods are the most frequently used and partially prescribed by standards. Depending on country, however, other methods and measurement angles can be required.

The forwards scattered light-method, for example, at an angle of 12°, is not so frequently applied.

In the case of all described methods, there arises, however, the already described problem that reflections at the location of installation, thus, for example, by a tube, or pipe, wall, corrupt the measurement result. The user must attempt "to calibrate away" these undesired reflections, however, these tests require time and expense as well as being susceptible to error. The influence of the reflections depends on the turbidity. Usually, in real systems, the turbidity value cannot be varied as much as desired.

According to the invention, the sensor is calibrated before the actual installation at the location of installation and one or more calibration graphs 1 recorded.

In this regard, the sensor is calibrated multiple times under respectively different environmental conditions. Environmental conditions concern, for example, different materials and different diameters, respectively different wall separations. Most often, the sensors are applied in pipes, whose typical diameters range from DN10 to DN1000. The sensors can, however, also be applied in vats and the like; correspondingly, the wall separation can range, in such case, from 10 mm to 1000 mm. Depending on application and sensor, also smaller diameters or separations can be selected.

Typical materials are stainless steel, cast-iron, copper, polyethylene (PE), polyvinyl chloride (PVC), polypropylene (PP), brass, glass fiber reinforced plastics (GFP) and ceramics. Other environmental conditions include, for example, surface roughness, surface color, surface texture and/or accretions.

The calibrating with respectively different environmental conditions is performed for different turbidity values, for instance, from 0 FNU to 500 FNU. For example, at a first turbidity value, 0 FNU, with a first material and a first diameter, the turbidity value is recorded by the sensor. Then, in the case of the same material and same diameter, the turbidity value is increased, e.g. to 10 FNU, and, in turn, the measured value recorded. This is performed correspondingly for the mentioned turbidity range as well as the different environmental conditions.

The sole figure of the drawing shows a calibration graph 1 obtained thereby. The user selects then on-site its corresponding environmental conditions and, using the corresponding calibration curve suitable for its environmental conditions, adjusts the sensor (which, because of the reflections, is showing a wrong value) to the actual (true) turbidity value.

The calibration graph 1 is stored in a superordinated unit, for example, in a microcontroller, for instance, in tabular form, function, formula, graph or the like. The appropriate environmental conditions are selected by the user, for example, via the superordinated unit. The superordinated unit can be part of the turbidity sensor or it can be installed in an external device, especially in a transmitter. If the superordinated unit is installed in a transmitter, the turbidity sensor is connected with the transmitter via a galvanically isolated, especially inductive, interface. If the superordinated unit is in an external unit, the external unit can be, for instance, a mobile telephone, tablet, etc.

Shown on the x-axis of the calibration graph 1 is the turbidity value without adjusting $T_{without}$, while the y-axis gives the turbidity value with adjustment $T_{with}$.

If there are no wall effects, thus, for instance, in a fictive, infinitely large containment, the ideal curve 2 is obtained, which is shown with the dashed line.

Curve 3 (drawn gray) is for a containment of stainless steel. One can see that the adjustment is constant over a broad turbidity range and only at a very high turbidity value does curve 3 merge with the ideal curve, so that in the case of stainless steel pipes the influence cannot be neglected even at quite significant turbidity values. Curve 6 is likewise for a containment of stainless steel, however, in such case, the surface is polished. One can see that the influence is greater than in the case of unpolished stainless steel.

Curves 4 and 5 (drawn black) are for a plastic tube with different diameters, wherein the diameter of the tube of curve 4 is less. One can see that in the case of larger tubes, or pipes, (thus curve 5), the turbidity value is no longer influenced, once middle values of turbidity are reached, wherein, naturally, smaller tubes are influenced more than larger tubes.

SUMMARY OF REFERENCE CHARACTERS calibration graph
ideal curve without wall effects
curve with adjustment for stainless steel
curve with adjustment for plastic with a first diameter
curve with adjustment for plastic with a second diameter
curve with adjustment for stainless steel with polished surface
$T_{with}$ turbidity value with adjustment
$T_{without}$ turbidity value without adjustment

The invention claimed is:

1. A method for determining turbidity in a medium by means of at least one optical sensor, by taking into consideration wall effects as a function of environmental conditions at the location of installation of the sensor, comprising the steps of:
    sending transmission signals into the medium, wherein the transmission signals are converted into received signals by scattering with, the medium as a function of the turbidity;
    receiving the received signals; and
    converting the received signals into turbidity by taking into consideration wall effects as a function of environmental conditions at the location of installation,
    wherein the environmental conditions comprise at least different materials, different diameters of a calibration containment, or different distances of the optical sensor to a calibration containment; and
    adjusting the sensor based on a calibration graph corresponding to environmental conditions at the location of installation,
    wherein the calibration graph is recorded before the actual installation at the location of installation.

2. The method as claimed in claim 1, wherein the calibration graph is created by the steps of:
    calibrating the sensor multiple times with different environmental conditions, and
    wherein the calibrating is performed for different values of the turbidity; and
    recording calibration graphs corresponding to different environmental conditions;
    the corresponding environmental conditions of the location of installation are selected; and
    adjusting the sensor based on environmental conditions at the location of installation according to a corresponding calibration graph.

3. The method as claimed in claim 2, wherein:
the calibrating is performed for turbidity values from 0 FNU to 500 FNU.

4. The method as claimed in claim 2 wherein:
the materials include at least stainless steel, cast-iron, copper, polyethylene (PE), polyvinyl chloride (PVC), polypropylene (PP), glass fiber reinforced plastics (GFP), brass and ceramics.

5. The method as claimed in claim 2, wherein:
the environmental conditions further include surface roughness, surface color, texture of the surface and/or accretions.

6. The method as claimed in claim 2, wherein:
the diameter lies in the range of nominal diameters DN10 to DN1000,
or the distance of the optical sensor to the calibration containment lies in the range of values from 10 mm to 1000 mm.

7. A turbidity sensor for performing a method as claimed in claim 1.

8. The turbidity sensor as claimed in claim 7, having:
a superordinated unit, in which the calibration graphs are stored; and
through said superordinated unit the corresponding environmental conditions are selected, wherein:
said superordinated unit is part of the turbidity sensor or is installed in an external device.

9. The turbidity sensor as claimed in claim 8, wherein:
the turbidity sensor is connected with said transmitter via a galvanically isolated, interface.

10. The turbidity sensor as claimed in claim 8, wherein:
the external device is a transmitter.

11. The turbidity sensor as claimed in claim 9, wherein:
the galvanically isolated interface is an inductive interface.

* * * * *